United States Patent [19]

Karger et al.

[11] Patent Number: 4,778,909

[45] Date of Patent: Oct. 18, 1988

[54] STABLE SILICA-BASED ETHER BONDED PHASES FOR BIOPOLYMER SEPARATIONS

[75] Inventors: Barry L. Karger, Chestnut Hill; Binyamin Feibush, Needham; Neil T. Miller, West Newton; Alvaro Figueroa, Boston, all of Mass.

[73] Assignee: Northeastern University, Boston, Mass.

[21] Appl. No.: 609,272

[22] Filed: May 11, 1984

[51] Int. Cl.$^4$ .......................... C07F 7/08; C07F 7/18; C07F 7/10

[52] U.S. Cl. ..................................... 556/450; 556/416; 556/418; 556/419; 556/422; 556/423; 556/445; 556/448; 556/457; 556/458; 528/34; 528/39

[58] Field of Search ............... 556/416, 419, 423, 422, 556/418, 445, 448, 450, 457, 458; 528/34, 39

[56] References Cited

U.S. PATENT DOCUMENTS

| 2,796,406 | 6/1957 | Zorensen | 556/445 X |
| 2,846,458 | 8/1958 | Haguska | 556/445 |
| 3,172,899 | 3/1965 | Bailey | 556/445 |

Primary Examiner—Paul F. Shaver
Attorney, Agent, or Firm—Weingarten, Schurgin, Gagnebin & Hayes

[57] ABSTRACT

Fast high resolution separations of biopolymers with retention of biological activity have been achieved by hydrophobic interaction chromatography using trialkoxy silyl ethers of the general formula $$(RO)_3Si-(CH_2)_m-O-(CH_2CH_2O)_n-(CH_2)_pR'$$

chemically bonded to silica-based chromatographic supports. In the formula R is alkyl of from one to five carbons, m is an integer from two to five, n is an integer from one to five, p is an integer from zero of ten, and R' is methyl, phenyl, or substituted phenyl. Stable and reproducible bonded phases are prepared in a novel solventless procedure by a bonding process which uses a defined and controlled amount of water on the silica surface and a gaseous or volatile basic catalyst such as ammonia to produce a controlled amount of silane polymerization and cross-linking in addition to extensive bonding between silane and silica. High performance liquid chromatography on such weakly hydrophobic stationary phases using aqueous eluents and decreasing salt gradients under mild conditions permits high speed, high resolution separations of biopolymers such as proteins without destruction of their biological activity and without column degradation. Size exclusion chromatography can also be performed on these phases using low ionic strength eluents.

19 Claims, 7 Drawing Sheets

FIG. 6
CHROMATOGRAPHY OF PROTEINS
COMMERCIALLY-AVAILABLE SERUM SAMPLE

FIG. 7
CHROMATOGRAPHY OF PROTEINS
PAPAIN

FIG. 12

STABLE SILICA-BASED ETHER BONDED PHASES FOR BIOPOLYMER SEPARATIONS

FIELD OF THE INVENTION

This invention relates to stationary phases for liquid chromatography, and more particularly, to silica-based silyl ether stationary phases for hydrophobic interaction and size exclusion chromatography, and to improved methods for bonding silanes to silica.

BACKGROUND OF THE INVENTION

The separation of biopolymers such as proteins, polynucleotides, carbohydrates and peptides is important in the purification and analysis of such materials, in facilitating biochemical investigations, in medical testing and diagnosis, and in the genetic engineering/biotechnology fields.

In the past, such materials have been separated by traditional chromatographic techniques, including size exclusion chromatography (SEC) and hydrophobic interaction chromatography (HIC) on gel-type chromatographic supports. Such systems provide some resolution, but separation times are long because only low pressure can be used for mobile phase flow. In particular, the supporting gels cannot be subjected to high pressures to speed the flow of mobile phase.

Some attempts have been made to use modern high performance reversed phase liquid chromatography (RPLC) for the separation of such biopolymeric materials, to take advantage of the high speed and high resolution afforded by the sturdy small-particle silica-based chromatographic column packing materials employed in this technique. These attempts have shown some limited success, but have generally failed with mixtures of biopolymers because the biological materials either are irreversibly adsorbed to the strongly-hydrophobic stationary phases presently in use, e.g. n-alkyl, or can be removed only by mobile phases containing polar organic solvents and/or organic acids. Such harsh conditions frequently disrupt the quaternary, tertiary, and/or secondary structures of biopolymers, causing denaturation which destroys biological activity. They can also degrade chromatographic column packings.

Various attempts have been made to synthesize new chromatographic packing materials having stationary phases which bind biopolymers only weakly, so that they can be eluted under mild conditions which do not cause denaturation of the polymers or degradation of the chromatographic column packings. Covalently bonded stationary phases have been constructed using glycidyl ethers, glycidoxysilane derivatives, mixtures of glycidoxysilane derivatives and alkylsilanes, short-chain alkylsilanes, variously acylated polyaziridine, and ether-substituted silanes. All of these prior art phases suffer from one or more of the following deficiencies: they contain reactive and/or charged functional groups in the chromatographically-involved portion of the molecules, groups which can interact chemically with eluting solvents or with solutes being separated; they contain easily hydrolyzable linkages, and are therefore not chemically stable; they are too hydrophobic, and require polar organics for elution of proteins, conditions which are known to cause denaturation; and their hydrophobicity is difficult to adjust and control reproducibly.

An example of a silyl ether stationary phase precursor is $Cl_2(CH_3)Si-(CH_2)_3(CH_2CH_2O)_3CH_3$, disclosed by O. Schou and P. Larsen in *Acta. Chem. Scand.*, B 35, 337 (1981). This compound possesses on the silicon atom both a methyl group and a chain of five methylene ($CH_2$) units before the first oxygen atom, and thus when bonded to silica it produces a stationary phase too hydrophobic for hydrophobic interaction chromatographic separations of biopolymers such as proteins. This is shown in the reference by the author's use of the polar organic solvents methanol and tetrahydrofuran to elute a peptide mixture from a chromatographic column prepared with this bonded packing material.

Several approaches have been taken in designing and producing weakly hydrophobic silica-based bonded stationary phase chromatographic packings. In the simplest case, bonded stationary phases consisting of a single type of ligand are produced by one of two general bonding procedures to be discussed below. Although this is simple and straightforward, the hydrophobicity of the resulting bonded phases is limited by the availability of only a finite number of stationary phase precursors. Bonded phases containing mixtures of ligands have also been employed to balance and blend the properties of the several ligands to produce surface phases optimized for particular chromatographic purposes. Such mixed phases have been produced in two ways: by bonding a selected mixture of ligand precursors to silica in a single bonding step, or by a series of bonding steps and derivatization reactions which introduce various ligands and functionalities sequentially. The more popular sequential approach to bonded phase construction permits a variety of bonded phases to be produced, but is inherently irreproducible since organic reactions seldom go to completion or to precisely reproducible extents of reaction. Thus, if two or more successive reactions are employed to create a mixed bonded phase, later repetition of the sequence will produce a similar but non-identical mixed bonded phase.

The ligand precursors most commonly used in the prior art preparation of chemically bonded stationary phases have been glycidyl ethers, and reactive silanes which contain one to three halogen or alkoxyl groups on the silicon atom. The glycidyl ethers and monofunctional silanes can form only a single covalent bond with silica, thus producing bonded layers having inherently low stability. The bifunctional silanes create bonded layers of somewhat higher stability since they have the capacity to form more chemical bonds. Trifunctional silanes can, in principle, form the greatest number of bonds to the silica surface and hence would be expected to produce the most stable bonded coatings. However, trifunctional silanes have too frequently reacted irreproducibly to give bonded phases having low chromatographic utility as a result of having an excessively high loading of bonded phase as well as poor stabilities under chromatographic conditions. These problems are a result of uncontrolled polymerization and cross-linking of trifunctional silanes in the presence of excess water, a topic which will be discussed below.

Figure 1:
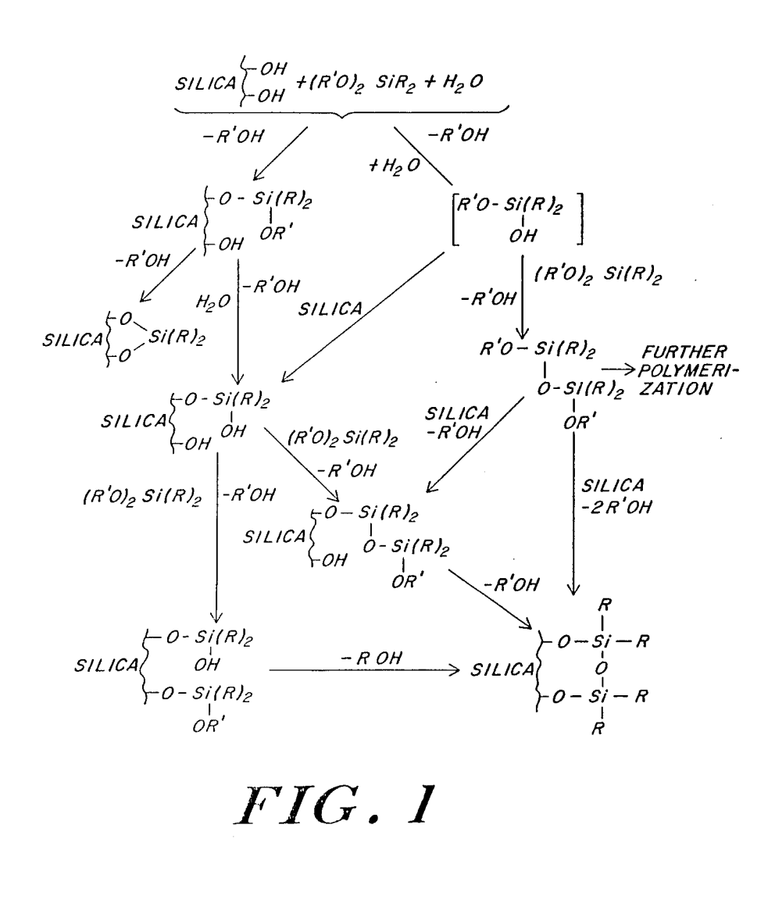
FIG. 1 is an illustration of some possible chemical structures which can result from the reaction of silica and a dialkoxy silane in the presence of water.

Two general bonding procedures have usually been employed to bond organosilanes to silica, depending on the sort of bonded layer to be produced. If the reaction between silica and organosilane is carried out under strictly anhydrous conditions, where the silica is dried by applying heat and vacuum and then refluxed with the organosilane in sodium-dried solvent, a monolayer of chemically bonded stationary phase is obtained. On the other hand, if the reaction between silica and a bifunctional or trifunctional organosilane is conducted in the presence of even a trace of water, some polymerization of the silane occurs, presumably via hydrolysis of some of the reactive functionalities of the silane to yield silanol groups which in turn react with additional organosilane reagent. Thus, if high loadings of bonded stationary phase are desired, the bonding procedure is conducted in the presence of water. FIG. 1 illustrates some of the sorts of structures which can form when a dialkoxy silane reacts with silica in the presence of water; all structures shown are present. The situation in the case of a trifunctional silane is similar but more complex. Such polymerization of organosilanes has in general been considered a problem, however, because it is frequently irreproducible and can cause overloading of the silica with bonded phase, thereby producing chromatographic packing materials having low surface area and poor porosity. In addition, bonded layers can be produced which are extensively polymerized but not extensively bonded to silica, with the result that if some of the silane-to-silica bonds are hydrolyzed, large patches of bonded phase can be lost and correspondingly large patches of unprotected silica surface can be exposed. Such stationary phases have been found to degrade rapidly and irreproducibly and to give irreproducible chromatography. As a result of these problems with uncontrolled polymerization and cross-linking when using trifunctional organosilanes, many workers have preferred, where possible, to use the mono or difunctional organosilanes in which such polymerization is either impossible or limited.

Two examples of atypical methods for bonding reactive organosilanes to silica are given by Larsson, and Majors. P. Larsson et al., *Advances in Chromatography,* 21, 41 (1983); R. Majors and M. Hopper, *J. Chromat. Sci.,* 12, 767, (1974). Larsson et al. refluxed a trialkoxy silane with carefully dried silica and a trace of triethylamine in carefully dried toluene. This procedure gives a monolayer of silane bonded to silica, with minimal polymerization and cross-linking, but creates the possibility of hydrolysis of unreacted alkoxy groups in subsequent handling or use of the packing material in the presence of water, with concomitant uncontrolled polymerization of silane at the silica surface and irreproducible chromatography. Majors equilibrated silica with water vapor in an atmosphere of low constant relative humidity, then slurried this with trialkoxysilane in dry toluene and slowly raised the temperature to the boiling point to complete the reaction. His procedure suffers in producing bonding reactions having relative standard deviations in reproducibility of surface converage as high as nine percent, and his bonded stationary phases are of undisclosed stability under chromatographic conditions. Further, both of the above processes employ a solvent, and differ from the process of the present invention in several respects.

In view of the above, it is clear that if biopolymer separations are to be performed in modern high performance liquid chromatographic instruments, by hydrophobic interaction chromatography and size exclusion, improved chromatographic packing materials are needed. Such improved packings in turn require new stationary phase precursors capable of providing stable bonded layers of stationary phases which are non-reactive and only weakly hydrophobic, and further require the development of improved bonding procedures which reproducibly yield uniform and stable layers of bound stationary phases.

SUMMARY OF THE INVENTION

The problems of fragile supporting gels and low flow rates, associated with traditional hydrophobic interaction chromatography, as well as the problems of column degradation and loss of biological activity in separated materials associated with reversed phase chromatography, are solved in the subject invention with a new class of silyl ether stationary phase precursors, and a new procedure involving several novel steps for bonding reactive organosilanes to silica reproducibly, to yield stable chromatographic supports.

More particularly, the present invention comprises trifunctional silyl ethers of the general formula $(RO)_3Si-(CH_2)_m-O-(CH_2CH_2O)_n-(CH_2)_p-R'$ where R is alkyl containing from one to five carbons, m is an integer from 2 to 5, n is an integer from 1 to 5, p is an integer from 0 to 10, and R' is methyl, or phenyl possibly substituted by one or more substituents such as hydrogen, lower alkyl, alkoxy, nitro, amino, amido, cyano, ester or halogen. Such compounds are bonded to silica to yield chemically stable weakly hydrophobic stationary phases useful for size exclusion chromatography and for hydrophobic interaction chromatographic separation of biopolymers such as certain proteins and polynucleotides.

The silyl ether stationary phase precursors produce bonded stationary phases which contain no reactive functional groups or hydrolyzable linkages in the chromatographically-involved portion of the molecules, and are therefore chemically stable and nonreactive toward eluents, and solutes being separated. In addition, the several hydrophilic ether linkages in the bonded phase chains reduce the hydrophobicity of hydrocarbon chains so that the stationary phases possess the required weakly hydrophobic character, permitting biopolymers to be recovered under mild elution conditions which do not cause denaturation. Finally, the hydrophobicity of the bonded phases can be adjusted for particular purposes by synthesizing various silyl ether bonded phase precursors according to the invention, or by employing mixtures of appropriate stationary phase precursors in varying proportions in the production of the bonded stationary phases.

The present invention further relates to a method for bonding organosilanes to silica, which comprises the steps of: placing a controlled amount of water on the surface of the silica particles to be coated, coating the surface of the silica particles uniformly with at least one alkoxysilane capable of forming at least two bonds with the silica surface via the silicon atom of the akloxysilane, and finally causing the alkoxysilane to react with the silica surface and crosslink and polymerize in a controlled manner, by heating the alkoxysilane-and-water-coated silica in the presence of vapors of a basic catalyst in the absence of solvent. The controlled amount of water on the silica is achieved by equilibrating the silica with the water vapor in an atmosphere of constant relative humidity above various saturated salt solutions or hydrated salts. The uniform coating of alkoxysilane is achieved by first dissolving the alkoxysilane in a volatile organic solvent which dissolves the alkoxysilane but does not cause it to migrate appreciably on silica of the type to be coated when the alkoxysilane is chromatographed on the silica using the organic solvent for elution, then adding this solution to the silica to be coated, and finally removing the solvent under reduced pressure or vacuum. Heating this water-and-alkoxysilane-coated silica in the presence of vapors of a basic catalyst such as ammonia causes bonding, polymerization, and cross-linking to take place in a controlled fashion to yield uniform stable bonded layers of stationary phase with high surface coverage. Running the bonding reaction in the absence of solvent ensures that the water and silane are located precisely on the silica surface where the bonding reaction is to occur, and that the reagents are available to the catalyst vapors. cl BRIEF DESCRIPTION OF THE DRAWINGS These and other features of the subject invention will be better understood in connection with the detailed description taken in conjunction with the drawing in which:

DETAILED DESCRIPTION OF THE INVENTION

Silyl ethers having the general formula $$(RO)_3Si-(CH_2)_m-O-(CH_2CH_2O)_n-(CH_2)_pR'$$

have been found to produce weakly hydrophobic stationary phases useful for liquid chromatography when chemically bonded to silica. The chromatographic supports thus formed are used in modern high performance liquid chromatographic instruments to separate mixtures of biopolymers such as proteins and polynucleotides by size exclusion chromatography using low ionic strength eluents, and by hydrophobic interaction chromatography using descending salt gradients, aqueous eluents, and mild conditions which do not cause denaturation of the biopolymers or degrade the column packing material.

In the above structural formula R is alkyl of from one to five carbons; m is an integer from 2 to 5, preferably 3; n is an integer from 1 to 5, preferably 2; p is an integer from 0 to 10, preferably 0 to 3; and R' is methyl, or phenyl possibly substituted by one or more substituents such as lower alkyl, alkoxy, nitro, amino, amide, cyano, ester or halogen. The $(CH_2)_m$ and $(CH_2)_p$ portions of the molecule can be straight chains as shown in the formula, but may also carry one or more branching substituents where hydrogen atoms have been replaced by methyl groups. It will be appreciated that the silyl ethers of the invention may be variously substituted to give derivatives which have chromatographically useful properties. It will also be appreciated that difunctional silyl ethers analogous to the trifunctional silyl ethers of the present application, but differing in having only two alkoxy groups on the silicon and having the third valence of the silicon occupied by an alkyl group, will bond to silica to give stationary phases useful for hydrophobic interaction and size exclusion chromatography, and will function in the bonding procedure of this application.

Preparation of Trialkoxy Silyl Ethers

The trialkoxy silyl ethers of the invention are prepared as follows from commercially available starting materials by known chemical reactions:

In the first step a Williamson Ether Synthesis is used to prepare an unsaturated ether according to the reaction $$CH_2=CH-(CH_2)_{m-2}-O-(CH_2CH_2O)_n-(CH_2)_pR'$$

where R', m, n, and p are as defined above. References: S. Patai, Ed.,"The Chemistry of the Ether Linkage," Interscience, N.Y., p. 446-450 and 460-468 (1967); B. Feibush, et al., J. Chromatog., 282, 3 (1983).

In a second step the unsaturated ether is caused to react with a trialkoxy silane in the presence of chloroplatinic acid catalyst according to the equation $$(RO)_3Si-(CH_2)_m-O-(CH_2CH_2O)_n-(CH_2)_pR'$$

where R, m, n, p, and R' are as defined above. Reference: J. L. Speier, J. A. Webster, and G. H. Barnes, J. Amer. Chem. Soc., 79, 974 (1957).

For the case in which m in the final product is two, the desired compound is prepared according to U.S. Pat. No. 2,835,690 from a trialkoxyvinylsilane and the appropriate alcohol:

$$(RO)_3Si-(CH_2)_2-O-(CH_2CH_2O)_n-(CH_2)_p-R'$$

Using the described synthetic methods, trialkoxy silyl ethers of the general formula $(RO)_3Si-(CH_2)_m-O-(CH_2CH_2O)_n-(CH_2)_pR'$, where R, m, n, p, and R' are as listed below have been synthesized:

TABLE I

Trialkoxy Silyl Ethers Prepared

| Compound No. | R | m | n | p | R' |
|---|---|---|---|---|---|
| 1 | ethyl | 3 | 1 | 0 | methy |
| 2 | ethyl | 3 | 2 | 0 | methyl |
| 3 | ethyl | 3 | 3 | 0 | methyl |
| 4 | ethyl | 3 | 2 | 1 | methyl |
| 5 | ethyl | 3 | 2 | 3 | methyl |

Preparative Examples

The preparations given below were made using commercially available starting materials. Suppliers for such chemicals are indicated below: The compounds 2-methoxy ethanol, diethyleneglycol monomethyl ether, and diethyleneglycol monobutyl ether were purchased from Fluka Chemical Co., 255 Oser Avenue, Hauppauge, New York, 11788. Olin Chemicals Group, 275 Winchester Avenue, P.O.Box 30-275, New Haven, Conn. 06511, supplied triethyleneglycol monomethyl ether. Allyl bromide was purchased from Sigma Chemical Co., P.O. Box 14508, St. Louis, Mo. 63178. Petrarch Systems, Inc., Bartram Road, Bristol, Pa. 19007, supplied triethoxy silane.

EXAMPLE 1

Preparation of 4,7 - Dioxaoctyl -1- triethoxysilane (1)

A. Preparation of 1 - Allyloxy-2-methoxyethane (1A)

Sodium (6.05 g, 263 mmoles) was placed in 250 mL of dry toluene (distilled from sodium) in a dry 500 mL flask and 2-methoxyethanol (20.9 mL, 265 mmoles) was added at a fast dropping rate. The solution was stirred 1 hour at room temperature, refluxed for 12 hours, then cooled in an ice bath. Allyl bromide (22.0 mL, 260 mmoles) was added and the mixture was stirred for 1 hour, heated at reflux for about 30 minutes, cooled, and a small amount of methanol was added to decompose unreacted sodium. After filtering the sodium bromide precipitate and concentrating the filtrate, the product was chromatographed on silica gel (eluents: toluene, then 2.5% ethyl acetate in toluene) then purified by azeotropic distillation of the toluene with methanol followed by fractional distillation to produce a 50% yield of colorless liquid, b.p. 120°-121° C. Thin layer chromatography on silica gel using 15% ethyl acetate in toluene showed one spot at $R_f=0.50$ using phosphomolybdic acid spray detection.

$^1$H NMR : $\delta 3.30$ (s,OCH$_3$); 3.61 [m,W$_{\frac{1}{2}}=3$Hz(CH$_2$CH$_2$O)]; 4.04 (d,J=5.5 Hz, CH$_2$ allyloxy); 5.0–5.5(m, CH$_2$ vinyl); 5.6–6.3 (m, CH vinyl).

B. Preparation of Silane (1)

A sample of 1A (15.0 g, 130 mmoles) was dissolved in 20 mL of chloroform and stirred for 15 minutes. To this solution was added triethoxysilane (36.6 mL, 195 mmoles) followed by a few crystals of hexachloroplatinic acid. The mixture was refluxed for about 2 hours, then volatiles were removed under reduced pressure (1 torr) at room temperature. Fractional distillation produced a 90% yield of colorless liquid, b.p. 99°-100° C. at 0.6 torr.

$^1$H NMR : $\delta 0.43-0.90$(m,Si—CH$_2$); 1.22 (t, J=7.0 Hz Si—O—C—CH$_3$); 1.32-2.04 (m,Si—C—CH$_2$); 3.34 (s, OCH$_3$); 3.41 [m, W$_{\frac{1}{2}}=3$Hz (CH$_2$CH$_2$O)$_1$CH$_2$]; 3.79(q, J=7.0 Hz, Si—O—CH$_2$).

EXAMPLE 2

Preparation of 4,7,10-Trioxaundecyl-1-triethoxy silane (2)

A. Preparation of 1-Allyloxy-2-(2'-methoxyethoxy) ethane 2A)

All procedures were the same as for preparation of 1A except that diethylene glycol monomethyl ether (31.2 mL, 265 mmoles) was used. After filtering the sodium bromide precipitate and concentrating the filtrate, the product was chromatographed on silica gel (eluents 5% ethyl acetate in toluene followed by 15% ethyl acetate in toluene) and then purified by fractional distillation to produce a 62% yield of colorless liquid, b.p. 49° C. at 1.5 torr. Thin layer chromatography on silica gel using 60% ethyl acetate in toluene showed one spot, $R_f=0.61$ using phosphomolybdic acid (3% in ethanol) spray detection. Gas chromatography on a 2 m x 2 mm id glass column packed with 80-100 mesh Chromosorb W-HP coated with 3% OV-17 showed 1 peak at 5.10 minutes. Chromatographic conditions: N$_2$ flow 20 mL/min., injector 150° C., flame ionization detector 250° C., temperature programmed 60° C. to 150° C. at 4° C./min.

$^1$H NMR as under 1A, except $\delta 3.64$ [m, W$_{\frac{1}{2}}=4$ Hz, (CH$_2$CH$_2$O)$_2$].

B. Preparation of Silane (2)

All procedures were the same as for preparation of compound 1 except that a sample of 2A (25.3 g, 160 mmoles) was used. Fractional distillation produced an 82% yield of colorless liquid, b.p. 127°-8° C. at 1.5 torr.

$^1$H NMR as under 1 except $\delta 3.53$ [m, W$_{\frac{1}{2}}=4$ Hz (CH$_2$CH$_2$O)$_2$ CH$_2$].

Elemental Analysis: Calculated: 51.85%C, 9.88%H; Observed: 50.74%C, 9.64%H.

EXAMPLE 3

Preparation of 4,7,10,13-Tetraoxatetradecyl-1-triethoxysilane (3)

A. Preparation of 4,7,10,13-Tetraoxatetradec-1-ene (3A)

All procedures were the same as for preparation of 1A except that triethylene glycol monomethyl ether (41.6 mL, 265 mmoles) was used. After filtering the sodium bromide precipitate and concentrating the filtrate, the product was chromatographed on silica gel (eluents: toluene, 2.5% ethyl acetate in toluene, then 15% ethyl acetate in toluene) to produce a 65% yield of a colorless liquid. TLC on silica gel using 60% ethyl acetate in toluene showed one spot, Rf=0.53 using phosphomolybdic acid spray detection.

$^1$H NMR as for 1A except $\delta 3.59$ [m, W$_{\frac{1}{2}}=5$Hz, (CH$_2$CH$_2$O)$_3$].

B. Preparation of Silane (3)

All procedures were the same as for preparation of compound 1 except that a sample of 3A (10.0 g, 49 mmoles) was used. Fractional distillation produced a 92% yield of colorless liquid, b.p. 142° C. at 1.0 torr.

$^1$H NMR as under 1 except $\delta 3.42$ [m, W$_{\frac{1}{2}}=6$ Hz, (CH$_2$CH$_2$O)$_3$CH$_2$].

Elemental Analysis: Calculated: 52.17%C, 9.78%H; Observed: 51.44%C, 9.68%H.

EXAMPLE 4

Preparation of 4,7,10-Trioxadodecyl-1-triethoxysilane (4)

A. Preparation of 1-Allyloxy-2-(2'-ethoxyethoxy) ethanol (4A)

All procedures were the same as for preparation of 1A except that diethylene glycol monoethyl ether (39.0 mL, 0.288 mmoles) was used. After filtering the sodium bromide precipitate and concentrating the filtrate, the product was chromatographed on silica gel (eluents: toluene, 15% ethyl acetate in toluene, then 50% ethyl acetate in toluene) and then purified by fractional distillation to produce an 80% yield of colorless liquid, b.p. 78°–79° C. at 0.2 torr.

$^1$H NMR :$\delta$1.02 (t, J=7.0 Hz, —O—C—CH$_3$); 3.28 (q, J=6.5 Hz, —O—CH$_2$C); 3.30 [m, W$_{\frac{1}{2}}$=4 Hz (CH$_2$CH$_2$O)$_2$]; 3.77 (d, J=5.0 Hz, CH$_2$ allyloxy); 4.69-5.22 (m, CH$_2$ vinyl); 5.29-6.02 (m, CH vinyl).

B. Preparation of Silane (4)

All procedures were the same as for preparation of compound 1 except that a sample of 4A (20.0 g, 230 mmoles) was used. Fractional distillation produced a 91% yield of a colorless liquid, b.p. 146°–7° C. at 1.2 torr.

$^1$H NMR :$\delta$0.17-0.64 (m, Si—CH$_2$); 0.97 (t, J=7.0 Hz, Si—O—C—CH$_3$ and —O—C—CH$_3$); 1.25-1.78 (m, Si—C—CH$_2$); 3.27 (q, J=7.0 Hz, OCH$_2$—C); 3.34 [m, W$_{\frac{1}{2}}$=4 Hz (CH$_2$CH$_2$O)$_2$CH$_2$]; 3.55 (q, J=7.0 Hz, Si—O—CH$_2$).

EXAMPLE 5

Preparation of 4,7,10-Trioxatetradecyl-1-triethoxysilane (5)

A. Preparation of 1-Allyloxy-2-(2'-butoxyethoxy) ethanol (5A)

All procedures were the same as for preparation of compound 1 except that diethylene glycol monobutyl ether (45.3 mL, 260 mmoles) was used. After filtering the sodium bromide precipitate and concentrating the filtrate, the product was chromatographed on silica gel (eluents: toluene, 2.5% ethyl acetate in toluene, then 5% ethyl acetate in toluene), to produce a 60% yield of colorless liquid.

$^1$H NMR :$\delta$0.52-1.06 (m, O—C—C—C—CH$_3$); 1.06-1.82 (m, O—C—CH$_2$CH$_2$—C); 3.42 (q, J=6 Hz, —O—C—C—CH$_2$—C); 3.53 [m, W$_{\frac{1}{2}}$=4 Hz, (OCH$_2$CH$_2$)$_2$]3.94 (d, J=5.0 Hz, CH$_2$ 4.86-5.39 (m, CH$_2$ vinyl); 5.46-6.19 (m, CH vinyl).

B. Preparation of Silane (5)

All procedures were the same as for preparation of compound 1 except that a sample of 5A (10.0 g, 50 mmoles) was used. Fractional distillation produced an 80% yield of colorless liquid, b.p. 150° C. at 1.0 torr.

$^1$H NMR :$\delta$0.37-2.02 (m, Si—CH$_2$CH$_2$—C, —O—C—CH$_2$—CH$_2$—C); 1.17 (t, J=7.0 Hz, Si—O—C—CH$_3$ and —O—C—C—C—CH$_3$); 3.43 (q, J=6.0 Hz, —O—CH$_2$—C—C—C); 3.53 [m, W$_{\frac{1}{2}}$=4.0 Hz (CH$_2$CH$_2$O)$_2$CH$_2$]; 3.73 (q, J=7.0 Hz, Si—O—CH$_2$—C).

Bonding Process

The bonding process for attaching the trialkoxy silyl ether to silica to form a stable weakly hydrophobic bonded stationary phase for liquid chromatographic separations of biopolymers includes the following steps:

1. Equilibrating the silica to be coated in an atmosphere of constant relative humidity.

The purpose of this step is to assure a constant controlled amount of water on the silica surface. Water is necessary later for hydrolysis of some alkoxyl groups of the alkoxy silanes to produce silanols which can react to give polymerization, cross-linking, and bonding to the silica surface. The amount of water must be constant from batch to batch if the extent of reaction of silane is to be controlled and reproducible. The relative humidity maintained during the equilibration step is not critical. It is convenient to equilibrate the silica at 15% relative humidity over a saturated solution of lithium chloride, but other humidities, obtained over solutions of other salts or in other ways, are also feasible. Equilibration time is not critical so long as equilibrium is reached. Times in the range from 4 days to two weeks are generally sufficient. Temperature of equilibration is not critical, and room temperature is generally used. The amount of water on the silica surface should be constant from batch to batch, and preferably be in the range from about 10 to about 40 micromoles per square meter of the silica's surface.

2. Transferring the water-equilbrated silica to an ampoule or small flask which can be evacuated as desired in later steps.

3. Adding the silane stationary phase precursor in a volatile solvent which dissolves the silane but does not move it appreciably when one attempts to chromatograph the silane on silica of the sort to be coated using the solvent for elution.

Selecting the solvent in this way ensures that after removal of the solvent in the solvent removal step below the silica will be uniformly coated with the silane. If the solvent were to move the silane on the silica during attempted chromatography, then as the solvent was removed in the step below the silane would tend to migrate to those parts of the silica surface from which the last droplets of solvent were evaporating, producing an uneven coating of silane.

The amount of silane used should be related to the number of silanols on the surface of the silica being coated, and should constitute from an equivalent amount to about a five-fold excess. As silica possesses theoretically about 8 micromoles of silanol groups per square meter of surface, this means that from about 8/3 to about 40/3 micromoles of silane per square meter of silica surface (reflecting 3 reactive alkoxyl groups per silane) is preferred. The amount of silane which ultimately bonds to the silica under our conditions is not strongly dependent on the amount of silane added.

4. Mixing the silane and silica in the selected solvent.

5. Removing the solvent and some of the water under reduced pressure and finally with vacuum under controlled conditions, to leave a silica powder coated with silane and a defined amount of water.

Solvent removal leaves a uniform coating of silane and water on the surface of the silica particles, in position to react with the surface during the reaction step below. Prior art procedures generally conduct the bonding step in a refluxing solvent such as toluene, removing the water azeotropically from the surface of the silica before the silane can react properly with the silica surface. As a result, prior art bonding procedures go more slowly and less completely than the reaction under the conditions of the invention.

Some reaction may begin to take place at this stage of the procedure, but so long as the equilibration and solvent removal steps are constant in successive preparations, reproducibility of silane bonding and cross-linking are good.

By reduced pressure is meant a pressure less than atmospheric, generally 5–30 mm of mercury. By vacuum is meant a pressure of from 0.001 to 10 mm of mercury. The particular conditions for solvent removal depend on the solvent chosen.

6. Replacing the vacuum with vapors of a basic volatile liquid or a basic gas such as ammonia, which serves as a catalyst in the reaction.

The introduction of a basic catalyst is important to promote reaction between silanols and silane, between water and silane, and between silanols, both speeding the reactions and causing them to tend toward completion. The catalyst may be any basic material having a reasonably high vapor pressure at 100° C. Low molecular weight amines are operable and ammonia gas is preferred.

7. Sealing the ampoule.

8. Heating the sealed mixture of silane-coated silica and basic catalyst in the absence of solvent to cause the reaction producing extensive bonding between silane and silica, and controlled cross-linking between the silanes at the silica surface.

Most of the bonding reaction takes place in this step, many bonds forming between silane and silanols on the silica surface, and between silane groups bonded to the silica, ultimately giving a highly bonded and cross-linked surface coating which is quite stable. Reproducibility of the surface coating in successive batches results from the use of controlled constant amounts of water on the silica in the first step and the uniform coating of silane and water produced at the silica surface in the solvent removal step.

The temperature and time for the reaction are not critical but are related, lower temperatures requiring longer times, and conversely. Suitable temperatures are from about 50° C. to 200° C. and the time required is from several hours to several days. A temperature of 100° C. for 24 hours is convenient and preferred.

9. Cooling the ampoule.

10. Washing the treated silica to remove unreacted silane and reaction by-products.

Solvents which will dissolve the silane and by-products and which do not react with the bonded stationary phase or silica will serve. Successive washes with carbon tetrachloride, methylene chloride, and methanol are preferred.

11. Drying the treated silica in an inert atmosphere. Temperature and time are not critical. Drying at a temperature of about 60° C., for about 12 hours, under a nitrogen atmosphere is preferred.

Those skilled in the art will appreciate that not all these steps are essential, that some may be accomplished in other ways, that some of them can be combined, and the order of some may be reversed.

Preparative Examples

The following preparations of bonded stationary phase chromatographic packing materials were made with Vydac silica from The Separations Group, P.O. Box 867, 16640 Spruce Street, Hesperia, Calif. 92345, the silica having a surface area of 78 $m^2/g$, approximately 8 $\mu$moles of silanols/$m^2$. Carbon analyses were performed by Multi Chem Laboratories, Inc., 171 Lincoln Street, Lowell, Mass. 01851, according to the procedure 47.013 given in the 13th Edition of the Official Methods of Analysis of the Association of Official Analytical Chemists, William Horwitz, Ed., published by the Association of Official Analytical Chemists, Washington, D.C., 1980.

EXAMPLE 6

Preparation of Packing 1

Vydac silica (5.0062 g, 3.124 mmoles of silanols) was placed in an open dish in an atmosphere of 15% relative humidity over a saturated aqueous solution of lithium chloride in a closed container, and allowed to equilibrate for four days at 20° C. to establish a controlled amount of water on the silica surface. It was then transferred quickly to a thick-walled glass ampoule and a solution of 4,7-dioxaoctyl-1-triethoxy silane (silane 1, 1.75 mL, 6.25 mmoles)in hexane was added. The mixture was shaken until homogeneous, then solvent was removed by evaporation at room temperature on a rotary evaporator, followed by evaporation under vacuum (0.5 torr, room temperature) for about five hours. Ammonia gas was admitted, returning the pressure in a system to one atmosphere, then the ampoule was sealed and heated in an oven at 100° C. for 24 hours. After cooling and opening the ampoule, the coated silica was washed successively with carbon tetrachloride, methylene chloride, and methanol, then dried in an oven at 60° C. for about 12 hours in a helium atmosphere. Elemental analysis for carbon showed the coated silica contained 4.46%C, corrected for a blank value of 0.62%C in the silica gel used. This corresponds to 5.22 $\mu$moles/$m^2$ coverage assuming one bond between each silane and the silica and no polymerization or cross-linking of silane, or to 8.73 $\mu$moles/$m^2$ coverage, assuming all three alkoxyl groups of each silane have been lost through reaction with silica and/or polymerization and cross-linking.

EXAMPLE 7

Preparation of Packing 2

The procedure was the same as for preparation of packing 1 except that 10.0 g of silica (6.24 mmoles of silanols) was treated with 4.0 mL of 4,7,10-trioxaundecyl-1-triethoxy silane (silane 2, 12.3 mmoles) in methylene chloride. Corrected elemental analysis showed the coated silica contained 4.05% carbon, corresponding to between 3.91 and 5.88 $\mu$moles/$m^2$ coverage, depending on the sorts of bonding achieved.

EXAMPLE 8

Preparation of Packing 2A

The procedure was the same as preparation of packing 1 except that 2.5121 g of silica (1.567 mmoles of silanols) was treated with 1.0 mL of 4,7,10 trioxaudecyl-1-triethoxy silane (Silane 2, 3.09 mmoles) in methylene chloride. Corrected elemental analysis showed the coated silica contained 4.02% carbon, corresponding to between 3.88 and 5.83 $\mu$moles/$m^2$ coverage, depending on the sorts of bonding achieved.

EXAMPLE 9

Preparation of Packing 2B

The procedure was the same as for preparation of packing 1 except that 2.5084 g of silica (1.565 mmoles of silanols) was treated with 1 mL of 4,7,10-trioxaundecyl-1-triethoxysilane (silane 2, 3.09 mmoles) in methylene chloride. Corrected elemental analysis showed the coated silica contained 3.83% carbon, corresponding to between 3.68 and 5.53 μmoles/m² coverage, depending on the sorts of bonding achieved.

EXAMPLE 10

Preparation of Packing 3

The procedure was the same as for preparation of packing 1 except that 5.01 g of silica (3.126 mmoles of silanols) was treated with 2.30 mL of 4,7,10,13-tetraoxatetradecyl-1-triethoxysi(silane 3, 6.25 mmoles) in hexane. Corrected elemental analysis showed the coated silica contained 4.62% carbon, corresponding to between 3.87 and 5.42 μmoles/m² coverage, depending on the sorts of bonding achieved.

EXAMPLE 11

Preparation of Packing 4

The procedure was the same as for preparation of packing 1 except that 5.0061 g of silica ( 3.123 mmoles of silanols) was treated with 2.1 mL of 4,7,10-trioxadodecyl-1-triethoxysilane (silane 4, 6.21 mmoles) in hexane. Corrected elemental analysis showed the coated silica contained 4.32% carbon, corresponding to between 3.86 and 5.58 μmoles/m² coverage, depending on the sorts of bonding achieved.

EXAMPLE 12

Preparation of Packing 5

The procedure was the same as for preparation of packing 1 except that 10.2208 g of silica (6.377 mmoles of silanols) was treated with 4.7 mL of 4,7,10-trioxatetradecyl-1-triethoxysilan (silane 5, 12.8 mmoles) in hexane. Corrected elemental analysis showed the coated silica contained 5.89% carbon, corresponding to between 4.69 and 6.38 μmoles/m coverage, depending on the sorts of bonding achieved.

EXAMPLE 13

Preparation of Diluted Phase Packing

The procedure was the same as for preparation of packing 1 except that 5.2444 g of silica (3.272 mmoles of silanols) was treated with a mixture of 1.9187 g of 4,7,10-trioxaundecyl-1-triethoxysilane (silane 2, 5.92 mmoles) and 0.2402 g of 4,7,10-trioxatetradecyl-1-triethoxysilane (silane 5, 0.656 mmoles) in hexane. Corrected elemental analysis showed the coated silica contained 3.89% carbon.

Chromatography

The usual chromatographic conditions employed for use of the chromatographic packings of the present invention in hydrophobic interaction chromatography are:

Solvent A: 2M ammonium sulfate, 0.5M ammonium acetate, pH 6.
Solvent B: 0.5M ammonium acetate, pH 6.
Gradient: 0%B to 100%B, 20 min. linear gradient.
Detector: UV operating at 280nm, 0.1 AFS
Conditions: 1 ml/min. flow rate, 0.5cm/min. chart speed, T=25° C.

In the experiments and figures, these conditions were employed unless otherwise indicated.

Figure 2:
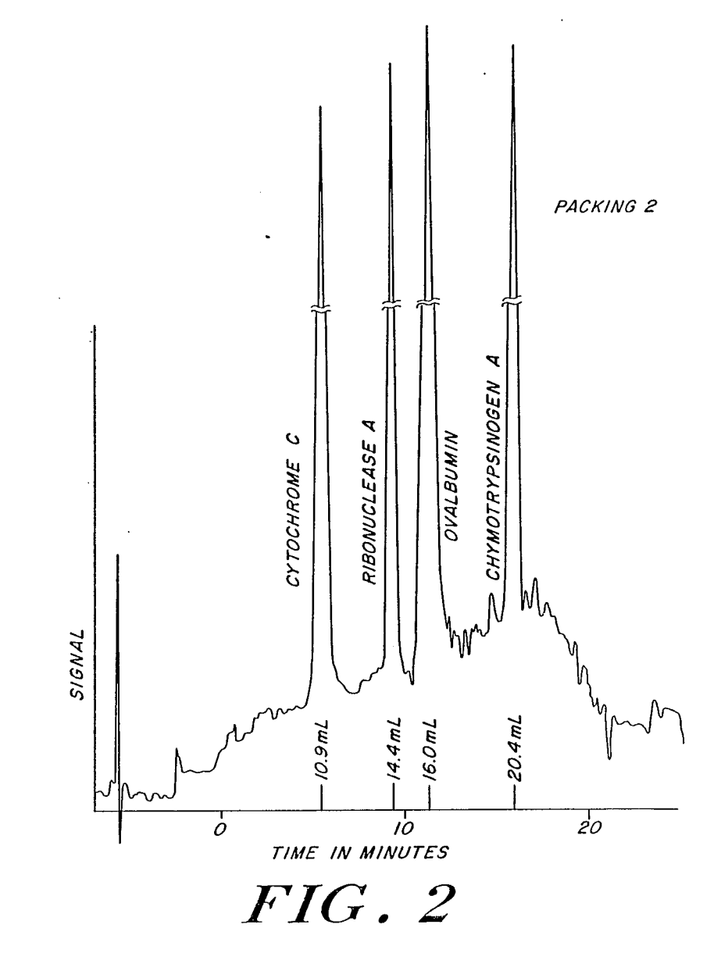
FIG. 2 illustrates separation of proteins by hydrophobic interaction chromatography on a bonded packing material of the invention.

FIG. 2 illustrates a separation of a protein mixture on bonded packing No. 2 under the above conditions.

Any salt may be used at any soluble concentration so long as it is compatible with the stationary phase and the materials being separated. Generally neutral salts are used in the pH range 2-7.

The anions and cations of neutral salts may be ranked by the Hofmeister or Lyotropic series according to their ability to "salt out" hydrophobic proteins from solution. Reference: P. H. von Hippel and T. Schleich, "Structure and Stability of Biological Macromolecules," S. N. Timasheff and G. D. Fasman, Eds., Marcel Dekker, p. 417 (1969). For example: for anions, sulfate exhibits a stronger salting out effect than acetate; for cations, sodium exhibits a stronger salting out effect than ammonium. Thus, it is predicted that a given concentration of sodium sulfate should "salt out" hydrophobic proteins more efficiently than ammonium acetate, and ammonium sulfate and sodium acetate should rank intermediately between the former salts.

In HIC, biopolymers which are most efficiently "salted out" of the mobile phase are retained to the greatest extent by the stationary phase, and conversely. Therefore, it would be expected that a given concentration of sodium sulfate should cause protein retention volumes to be greater than those obtained with an ammonium acetate salt solution, and ammonium sulfate and sodium acetate should result in protein retention volumes intermediate between the former salts. This is observed. Table II shows elution volumes of several proteins separated by HIC on a chromatographic packing of the invention using sodium sufate, ammonium acetate, and ammonium sulfate as the salt in the descending salt gradient, demonstrating the expected results.

TABLE II

| | Salt Effects in HIC of Proteins on Packing 2 Uncorrected elution volume, mL | | | |
|---|---|---|---|---|
| Salt | Cytochrome C | Ribonuclease A | Ovalbumin | Chymotrypsinogen A |
| Na₂SO₄ | 8.45 | 13.0 | 14.1 | 20.6 |
| (NH₄)₂SO₄ | 1.41 | 7.51 | 11.1 | 18.2 |
| NH₄OAc | All elute together at 1.14 mL. | | | |

Any temperature of operation may be used to aid the chromatography, limited only by the temperature stability of the biopolymers and by the freezing and boiling points of the mobile phase and compatibility with the stationary phase. As hydrophobic interactions are primarily entropy-driven, increases in temperature should increase them. Table III shows the results of a study of temperature effects in protein separations by HIC, which indicate that retention of each protein increases with temperatures, confirming the prediction.

TABLE III

| | Temperature Effects in HIC of Proteins on Packing 2 Uncorrected elution volume, mL | | | |
|---|---|---|---|---|
| T, °C. | Cytochrome C | Ribonuclease A | Ovalbumin | Chymotrypsinogen A |
| 10 | 1.15 | 4.66 | 9.51 | 16.3 |
| 25 | 1.37 | 7.35 | 10.9 | 18.1 |
| 40 | 1.73 | 8.74 | 12.0 | 19.7 |

Reproducibility of Preparation of Bonded Stationary Phases

That the above bonding procedure gives bonded stationary phases reproducibly is shown by the finding that three successive preparations of bonded stationary phases using Vydac silica gel and 4,7,10-trioxaundecyl-1-triethoxysilane (silane 2) gave products having 4.05%, 4.02%, and 3.83% carbon content, respectively, for a relative standard deviation of 3.0%. These figures are identical, within the experimental error of the carbon determination. Near identity of the columns prepared from these three separate batches of packing material is shown by the chromatographic results listed in Table IV below:

TABLE IV

Chromatographic Comparison of Replicate Batches of Packing Material Uncorrected elutin volume, mL

| Packing | Cyto-chrome C | Ribonuclease | Oval-bumin | Chymotryp-sinogen A |
|---|---|---|---|---|
| 2 | 10.7 | 14.3 | 15.9 | 20.1 |
| 2A | 10.4 | 14.1 | 15.3 | 19.9 |
| 2B | 10.1 | 13.9 | 15.0 | 19.8 |
| $\bar{X}$ | 10.4 | 14.1 | 15.4 | 19.9 |
| (RSD, %) | (2.88%) | (1.42%) | (2.98%) | (0.77%) |

Eluents:
A = 3.0 $\underline{M}$ ammonium sulfate, 0.5 $\underline{M}$ ammonium acetate, pH = 6.
B = 0.5 $\underline{M}$ ammonium acetate, pH = 6.
Other chromatographic conditions: as usual.

Stability

Figure 3:
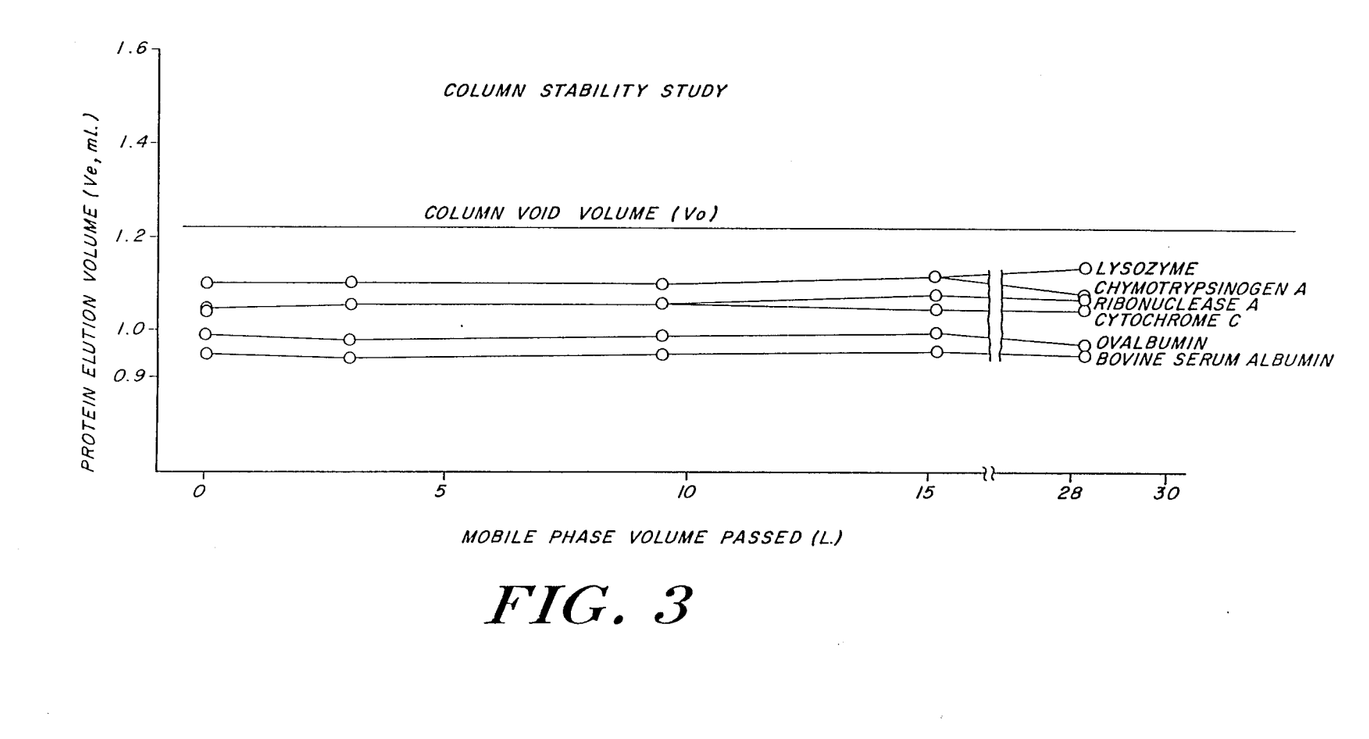
FIG. 3 illustrates the stability of a bonded packing material of the invention used long term under conditions of low salt mobile phase.

Stability of the bonded phases under chromatographic conditions was checked under conditions for SEC and HIC. In the first test, a column packed with 4,7,10-trioxaundecylsilyl-substituted Vydac (Packing 2) silica gel was set up in a continuous flow mode with 0.5M ammonium acetate mobile phase at pH=6 and T=40° C. This column was then removed from the flow system periodically and placed in a liquid chromatograph for testing. Injections of single proteins were made using mobile phases of 0.5M ammonium acetate, and elution volumes were recorded. With use of this approximate concentration of salt in the mobile phase, this column operates in the size exclusion chromatographic mode; proteins do not interact with the stationary phase. Therefore, if the column packing is stable over the course of the test, the proteins should exhibit consistent elution volumes less than the void volume of the column. On the other hand, if some hydrolysis of stationary phase occurs during the prolonged treatment of the column with 0.5M ammonium acetate mobile phase at pH=6, the basic proteins, i.e. those with pI>8 should begin to exhibit increasing elution volumes as the cumulative amount of mobile phase passed through the column increases, because proteins would begin to interact with uncovered silanol groups on the silica surface. Results are shown in FIG. 3, which reveals that the proteins tested maintained generally very consistent elution volumes, indicating the packing material was stable under conditions of the test.

Figure 4:
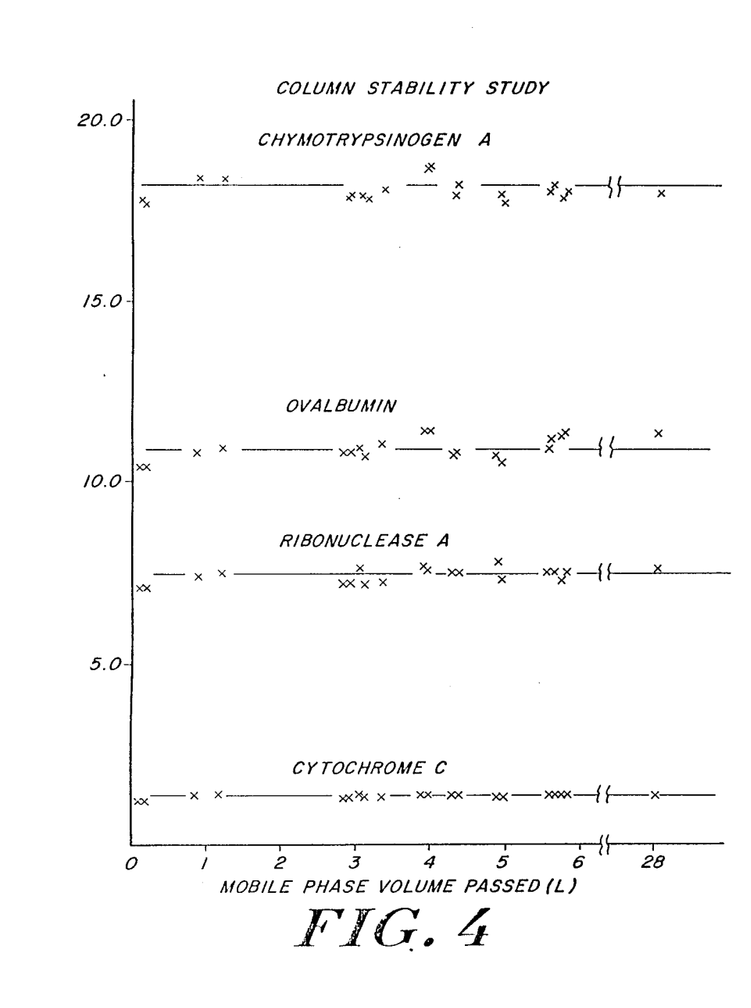
FIG. 4 illustrates the stability of a bonded packing material of the invention used long term under conditions of high salt mobile phase.

In the second test, based on HIC, the same column was operated with pH=6 mobile phase containing 2M ammonium sulfate plus 0.5M ammonium acetate at 25° C., and the total volume of mobile phase passed was monitored. Injections of proteins were made periodically and HIC was performed using the usual descending salt gradient. The results are shown in FIG. 4, which indicates that the elution volumes for the tested proteins remained constant within experimental error over the course of the test, indicating the column was stable and was not attacked by the high salt mobile phase.

In a third test, again based on HIC, the same column was operated with pH=6 mobile phase containing in this case 3$\underline{M}$ ammonium sulfate and 0.5$\underline{M}$ ammonium acetate alone. ammonium acetate at 25° C., and the total volume of mobile phase passed was monitored. Injections of proteins were made periodically and hydrophobic interaction chromatography was performed using a salt gradient descending from 3M ammonium sulfate and 0.5M ammonium acetate to 0.5M ammonium acetate alone. Table V below shows the uncorrected elution volumes and corresponding total mobile phase passed for the four proteins tested, indicating excellent reproducibility and hence column stability under high salt chromatographic conditions.

TABLE V

Column Stability Test Uncorrected $V_e$, mL

| Total mobile phase passed | Cyto-chrome C | Ribonu-clease A | Oval-bumin | Chymotryp-sinogen A |
|---|---|---|---|---|
| 85 | 10.7 | 14.2 | 15.5 | 20.1 |
| 150 | 10.7 | 14.2 | 15.5 | 20.2 |
| 880 | 10.9 | 14.4 | 16.0 | 20.3 |
| 980 | 10.8 | 14.3 | 15.9 | 20.1 |
| 1040 | 10.6 | 14.2 | 15.8 | 20.1 |
| 2050 | 11.2 | 14.5 | 16.2 | 20.3. |
| 2090 | 11.0 | 14.4 | 16.2 | 20.3 |
| 2900 | 11.2 | 14.4 | 16.1 | 20.3 |
| 3000 | 11.2 | 14.5 | 16.0 | 20.4 |
| 6900 | 11.1 | 14.5 | 16.2 | 20.5 |
| $\bar{X}$ | 10.9 | 14.4 | 15.9 | 20.3 |
| (RSD, %) | 2.13 | 0.88 | 1.68 | 0.66 |

In a fourth test another column of a different phase, namely 4,7,10,13-tetraoxatetradecylsilyl-substituted silica (Packing 3) was operated as in test 3 above with 3$\underline{M}$ ammonium sulfate and decreasing salt gradients from 3$\underline{M}$ ammonium sulfate and 0.5M ammonium acetate to 0.5$\underline{M}$ ammonium acetate alone at 25° C. The data in Table VI below confirm the results found in test 3 above and indicate that the bonding procedure yields phases that are very stable in use.

TABLE VI

Column Stability Test Uncorrected $V_e$, mL

| Mobile phase passed, mL | Cyto-chrome C | Ribonu-clease A | Oval-bumin | Chymotryp-sinogen A |
|---|---|---|---|---|
| 100 | 9.36 | 13.7 | 14.8 | 18.9 |
| 300 | 9.18 | 13.6 | 15.1 | 18.7 |
| 2000 | 9.43 | 13.7 | 15.0 | 18.7 |
| 5000 | 9.27 | 13.7 | 15.1 | 18.7 |
| 6000 | 9.45 | 13.9 | 15.3 | 19.3 |
| 7000 | 9.36 | 13.8 | 15.2 | 19.1 |
| $\bar{X}$ | 9.32 | 13.7 | 15.1 | 18.8 |
| RSD, | (1.13) | (0.98) | (1.68) | (1.03) |

Protein Mass and Activity Recovery

The bonded silyl ether chromatographic packings according to the invention do not adsorb proteins irreversibly and do not cause denaturation of biopolymeric materials when used in HIC mode. Egg white lysozyme was chromatographed on Packing 2 in HIC mode. Mass recovery studies showed recoveries in excess of 90%. The specific enzymatic activity of the recovered lysozyme fractions was determined. In all cases, the collected fractions were found to be enzymatically active. Specific activities were in general 20–40% higher than the standard, indicating that purification of lysozyme occurs on the columns, and that denaturation does not occur.

Further evidence supporting this conclusion is the findings that the fragile rat liver enzymes, carbamyl phosphate synthetase and ornithine transcarbamylase are not denatured when chromatographed on Packing 2 in HIC mode. Specific activities measured on the eluting peaks of these enzymes are in general 20% to 50% higher than those of the enzymes in the original sample, indicating that purification occurs on the columns, and that denaturation does not occur.

Chromatography of Proteins

Figure 5:
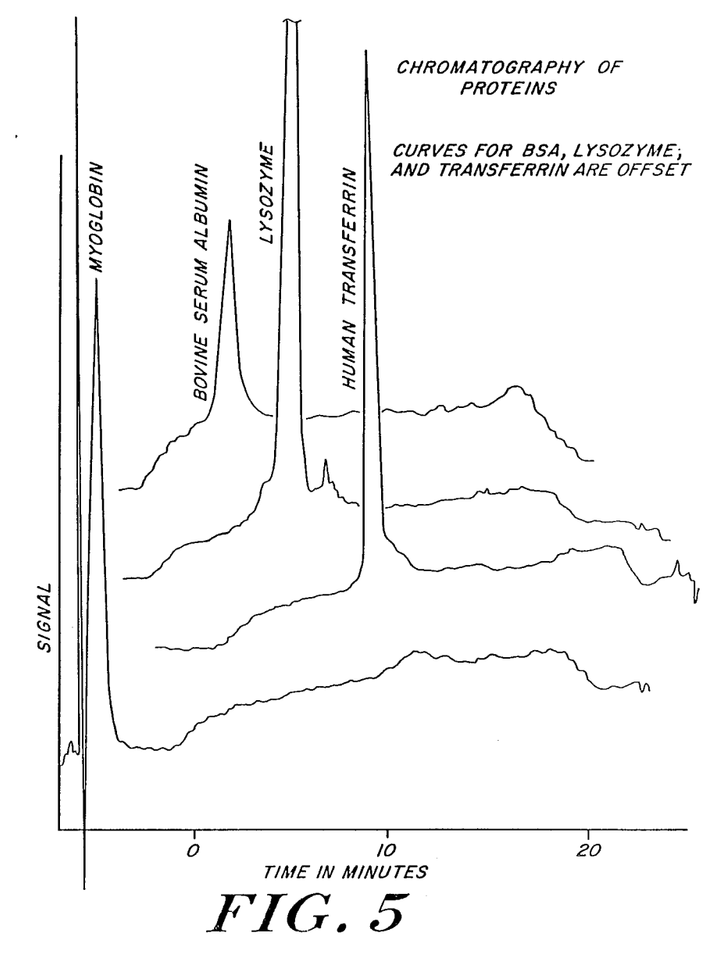
FIGS. 5 and 6 show the hydrophobic interaction chromatography of various proteins on bonded packing material No. 2 of the invention.
Figure 6:
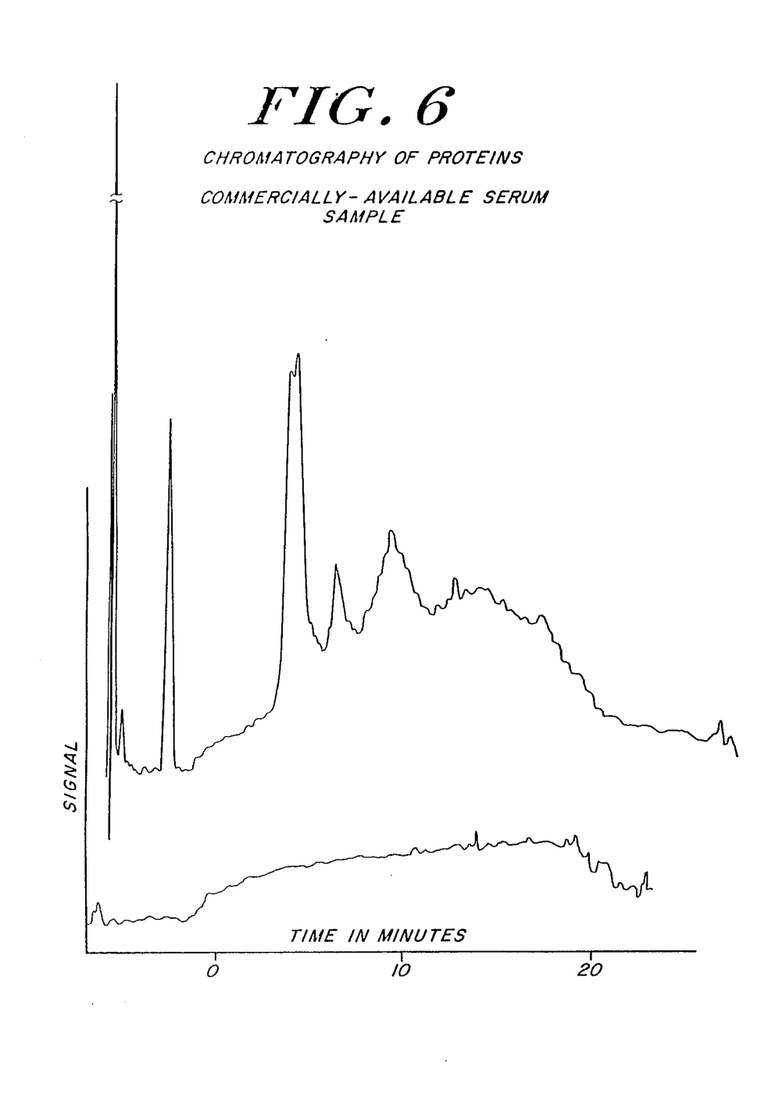
Figure 7:
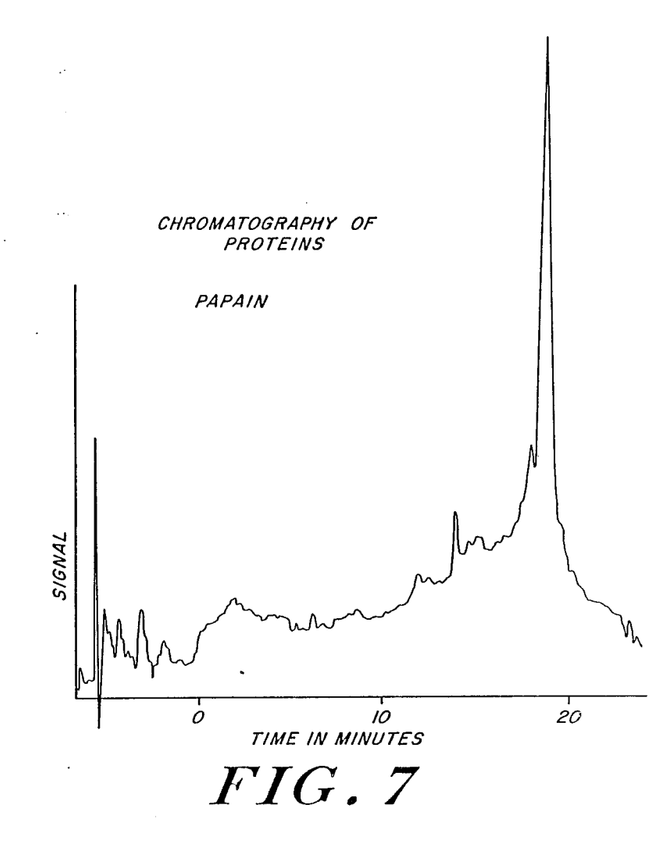
FIGS. 7-9 show the hydrophobic interaction chromatography of various proteins on bonded packing material No. 3 of the invention.
Figure 8:
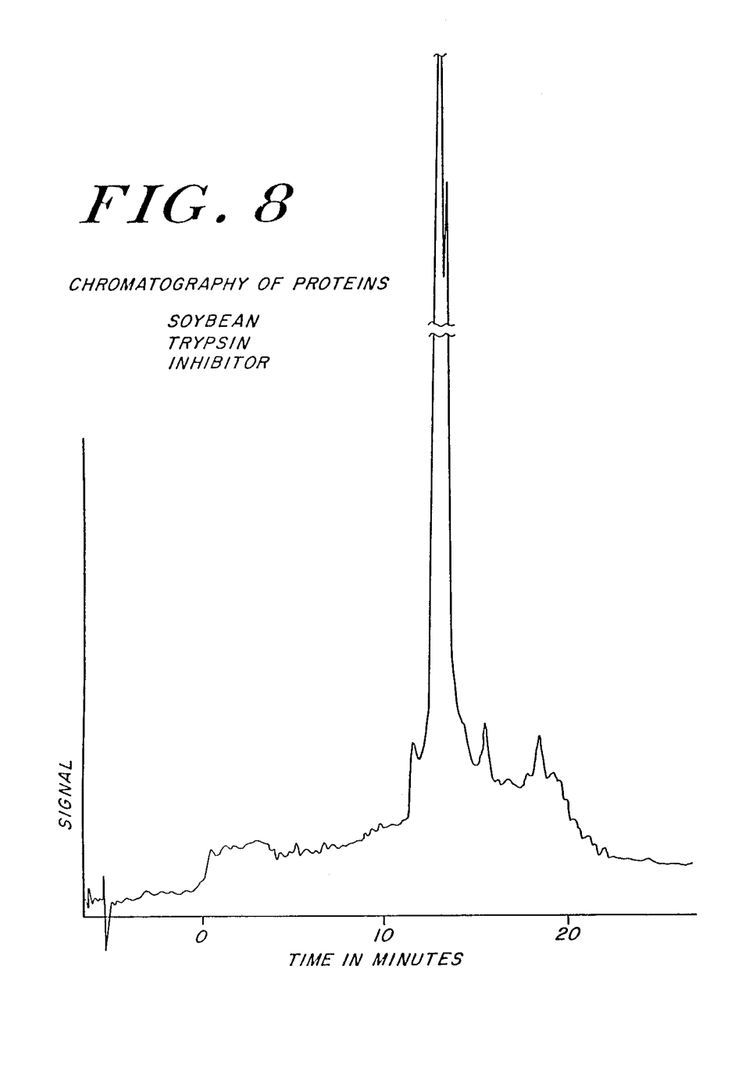
Figure 9:
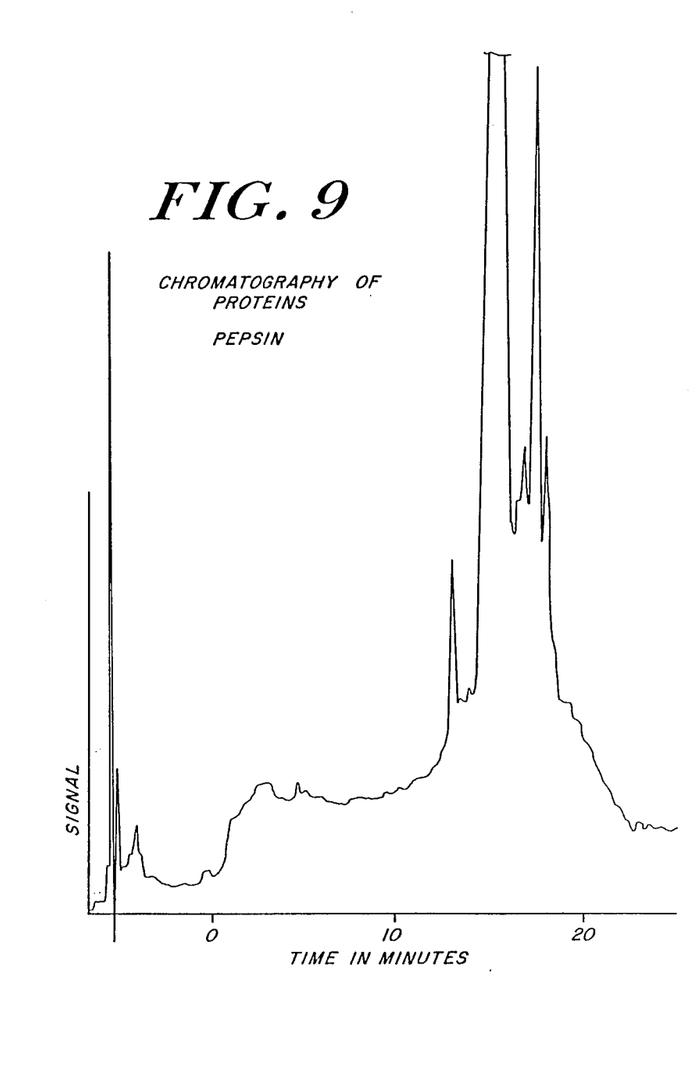

Various proteins were chromatographed in the HIC mode on the column of 4,7,10-trioxaundecylsilyl-substituted Vydac silica gel (packing 2), using the standard decreasing salt gradient. Results are shown in FIGS. 5 and 6. Similarly, a column of 4,7,10,13 tetraoxatetradecylsilyl-substituted silica (packing 3) was used for hydrophobic interaction chromatography of proteins, using a salt gradient of 3M ammonium sulfate/0.5M ammonium acetate decreasing to 0.5M ammonium acetate alone, all other conditions of chromatography being as usual. Results are shown in FIGS. 7-9. These chromatograms provide further evidence that the silyl ether phases and related bonded chromatographic packing materials are generally useful for separations of biopolymers such as proteins.

Mixtures of proteins have been separated on columns packed with several of the bonded phase packings of this invention to demonstrate the effects of variations in hydrophobicity. Hydrophobic interaction chromatography was carried out using a salt gradient of 3M ammonium sulfate/0.5M ammonium acetate decreasing to 0.5M ammonium acetate alone, all other chromatograhic conditions being as usual.

Results are shown in Table VII below:

TABLE VII

HIC Results on Columns on Varying Hydrophobicity
Uncorrected $V_e$, mL

| Packing | Cytochrome C | Ribonuclease A | Ovalbumin | Chymotrypsinogen A |
|---|---|---|---|---|
| 3(n = 3, p = 0) | 9.23 | 13.7 | 15.0 | 18.8 |
| 2(n = 2, p = 0) | 10.9 | 14.4 | 16.0 | 20.4 |
| 1(n = 1, p = 0) | 12.8 | 15.4 | 17.1 | 22.0 |
| 4(n = 2, p = 1) | 15.6 | 16.2 | 18.1 | 23.1 |

The most retentive phase, No. 4, gives incomplete recovies of Cytochrome C and Ovalbumin, indicating that it is too hydrophobic under these conditions.

Adjustment of Bonded Phase Hydrophobicity

The hydrophobicity of the bonded stationary phases of this invention can be adjusted by synthesizing various starting trialkoxy silyl ethers, and also by blending certain of these silyl ethers with other similar silyl ethers or with other trialkoxy silanes in various proportions prior to the bonding step. By thus mixing selected proportions of various trialkoxy silanes, then bonding them to silica, final bonded phases containing specified proportions of selected phases are produced.

Figure 10:
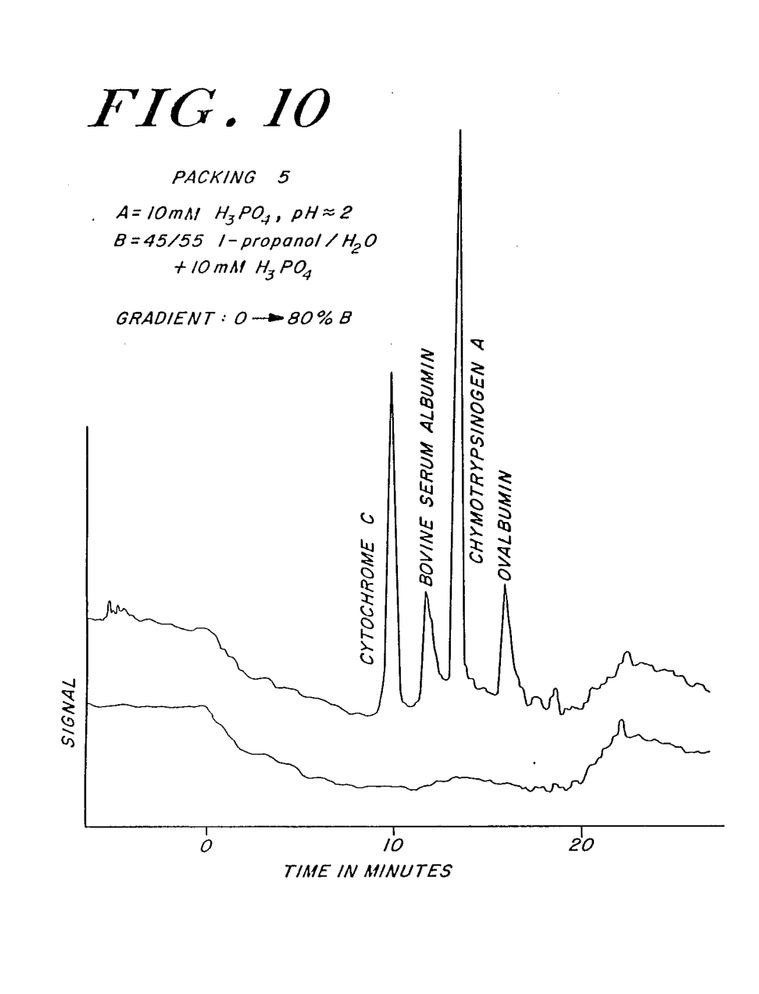
FIG. 10 illustrates the chromatographic behavior of a mixture of proteins on strongly hydrophobic bonded packing material No. 5 of the invention.

By way of example, when $(RO)_3Si-(CH_2)_3-O-(CH_2CH_2O)_2-(CH_2)_3CH_3$ bonded to silica the terminal n-butyl group was found to confer rather strong hydrophobicity to the stationary phase. As shown in FIG. 10, this material exhibited good separations of proteins using low pH, low ionic strength, and organic modifiers in the mobile phase, but under conditions of 0.5M ammonium acetate and pH=6, it was too hydrophobic, and gave a very poor separation of the same proteins.

"Diluted" Bonded Phases

Figure 11:
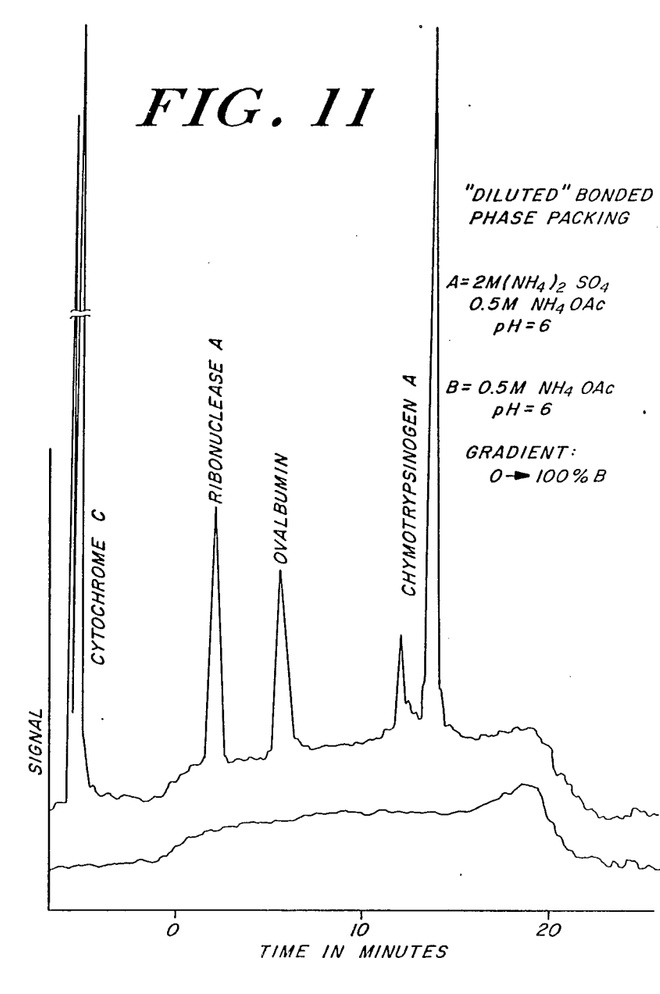
FIG. 11 illustrates the chromatographic performance of a "diluted" bonded packing material of the invention.

When the above phase was diluted with nine parts of the less hydrophobic phase $(RO)_3Si-(CH_2)_3-O-(CH_2CH_2O)_2-CH_3$ which terminates in a methyl group instead of a butyl group, and the mixture was bonded to silica, a diluted stationary phase was produced which was only weakly hydrophobic. It exhibited no retention of proteins under conditions of low pH, low ionic strength, and organic modifiers in the mobile phase. Under the conditions for HIC, however, with descending salt gradient, it exhibited a good separation of proteins as shown in FIG. 11. This demonstrates the possibility of adjusting the hydrophobicity of bonded phases by "diluting" hydrophobic phases with less hydrophobic phases. Conversely, the hydrophobicity of weakly hydrophobic phases can be increased by "diluting" with more strongly hydrophobic phases, then bonding the mixture to silica.

This "dilution" concept, using the rather weakly hydrophobic non-interacting silyl ethers of the present invention to space out the interactive groups in other stationary phases and thereby dilute their effects, is applicable to other sorts of liquid chromatography besides HIC. Examples of such other uses are in ligand exchange chromatography, in affinity chromatography, and ion exchange chromatography.

Size Exclusion

The silyl ether bonded chromatographic packings of this invention can be employed for size exclusion chromatography (SEC) simply by using a mobile phase which does not allow the materials being separated to interact with the silyl ether stationary phase. For proteins, such a mobile phase is 0.5M ammonium acetate at a pH of 6. Table VIII below lists a number of proteins which were chromatographed on a series of three columns of 4,7,10-trioxaundecylsilyl-substituted silica under conditions for SEC. The elution volumes generally decrease as the molecular weight increases, confirming that size exclusion chromatography is occurring.

TABLE VIII

Protein Elution Volume Data in the Size Exclusion Mode

| Solute | MW | log MW | pI | $V_e$ | [n] # mL/g | log(MW[n]) |
|---|---|---|---|---|---|---|
| KNO₃ | 101.1 | 2.00 | — | 3.44 mL | — | 2.00 |
| Uracil | 112.1 | 2.05 | — | 3.44 | — | 2.05 |
| Bovine pancreatic insulin | 11,500 | 4.06 | 5.35 | 3.23 | 3.2* | 4.26 |
| Equine cytochrome C | 12,200 | 4.09 | 10.6 | 2.92 | 3.2* | 4.59 |
| Bovine ribonuclease A | 13,700 | 4.14 | 9.4 | 2.95 | 3.3 # | 4.66 |
| Egg lysozyme | 14,000 | 4.15 | 11.0 | 3.04 | 2.7 # | 4.58 |
| Equine myoglobin | 17,500 | 4.24 | 7.1 | 2.92 | 3.1 # | 4.73 |
| Bovine trypsin | 23,000 | 4.36 | 10.8 | 2.97 | 3.2* | 4.87 |

TABLE VIII-continued

Protein Elution Volume Data in the Size Exclusion Mode

| Solute | MW | log MW | pI | $V_e$ | [n] # mL/g | log(MW[n]) |
|---|---|---|---|---|---|---|
| Bovine chymo-trypsinogen A | 25,500 | 4.41 | 9.5 | 2.97 | 2.5 # | 4.80 |
| Hog pepsin | 34,000 | 4.53 | <1.0 | 2.92 | 3.2* | 5.04 |
| Bovine β-lactoglobulin | 35,000 | 4.54 | 5.1 | 2.75 | 3.4 # | 5.08 |
| Hog pepsinogen | 40,000 | 4.60 | 3.7 | 2.84 | 3.2* | 5.11 |
| Egg ovalbumin | 44,000 | 4.64 | 4.7 | 2.78 | 3.2* | 5.15 |
| Bovine hemoglobin | 64,500 | 4.81 | 6.8 | 2.84 | 3.6 # | 5.37 |
| Bovnie serum albumin | 68,000 | 4.83 | 4.4-4.8 | 2.58 | 3.7 # | 5.40 |
| Human transferrin | 77,000 | 4.89 | 5.0 | 2.62 | 3.2* | 5.39 |
| Yeast hexokinase | 104,000 | 5.02 | 5-5.3 | 2.71 | 3.2* | 5.52 |
| Human γ-globulin | 160,000 | 5.20 | — | 2.49 | 3.2* | 5.71 |
| Beef catalase | 240,000 | 5.38 | 8.0 | 2.49 | 3.2* | 5.89 |
| Blue Dextran | 2,000,000 | 6.30 | — | 1.72 | — | — | pI values are taken from Karger, et al, Anal. Chem. 52 177(1980).
-intrinsic viscosity values [n] for native proteins are taken from C. Tanford, Adv. Protein Chem., 23,121 (1968).
*intrinsic viscosity values are estimated as the means of the known values reported by Tanford.
Chromatographic Conditions: Three coupled columns of packings 2, 2A and 2B, totaling 30 cm × 4.6 mm id.
Mobile phase = 0.5 M ammonium acetate; pH = 6.0; T = 25° C.; 280 nm UV 0.1 AFS; 0.5 mL/min.

Further evidence that size exclusion chromatography is occurring under these conditions is obtained by preparing a "universal calibration" curve using polystyrene standards, and plotting the various proteins on it for comparison. Data for polystyrene standards are given in Table IX below:

TABLE IX

Polystyrene Elution Volume Data*

| Standard | MW | [n] #mL/g | log(MW[n]) | $V_e$, mL |
|---|---|---|---|---|
| 1 | 800 | 1.73 | 3.14 | 3.20 |
| 2 | 2,000 | 3.17 | 3.80 | 3.09 |
| 3 | 4,000 | 5.01 | 4.30 | 3.02 |
| 4 | 9,000 | 8.55 | 4.89 | 2.88 |
| 5 | 17,500 | 13.26 | 5.37 | 2.67 |
| 6 | 35,000 | 20.96 | 5.87 | 2.43 |
| 7 | 50,000 | 26.52 | 6.12 | 2.30 |
| 8 | 100,000 | 41.90 | 6.62 | 2.03 |
| 9 | 233,000 | 73.23 | 7.23 | 1.80 |
| 10 | 300,000 | 86.52 | 7.41 | 1.76 |
| 11 | 600,000 | 136.71 | 7.91 | 1.71 |
| 12 | 900,000 | 178.66 | 8.21 | 1.71 |
| 13 | 1,800,000 | 282.29 | 8.71 | 1.71 |

*average of two determinations
-the intrinsic viscosity, [n], was calculated according to the Mark-Houwink equation: [n] = KM$^a$
where M = molecular weight
K, a = constants evaluated for specific conditions.
for atactic polystyrene,
M = 1 to 180 × 10$^4$
25° C. in dichloro ethane
K = 21.0 × 10$^{-3}$ mL/g
a = 0.66
Reference: J. Brandrup and E. H. Immergut, Eds., Polymer Handbook, 2nd Ed., J. Wiley & Sons, N.Y. (1975), p. IV-17.

Figure 12:
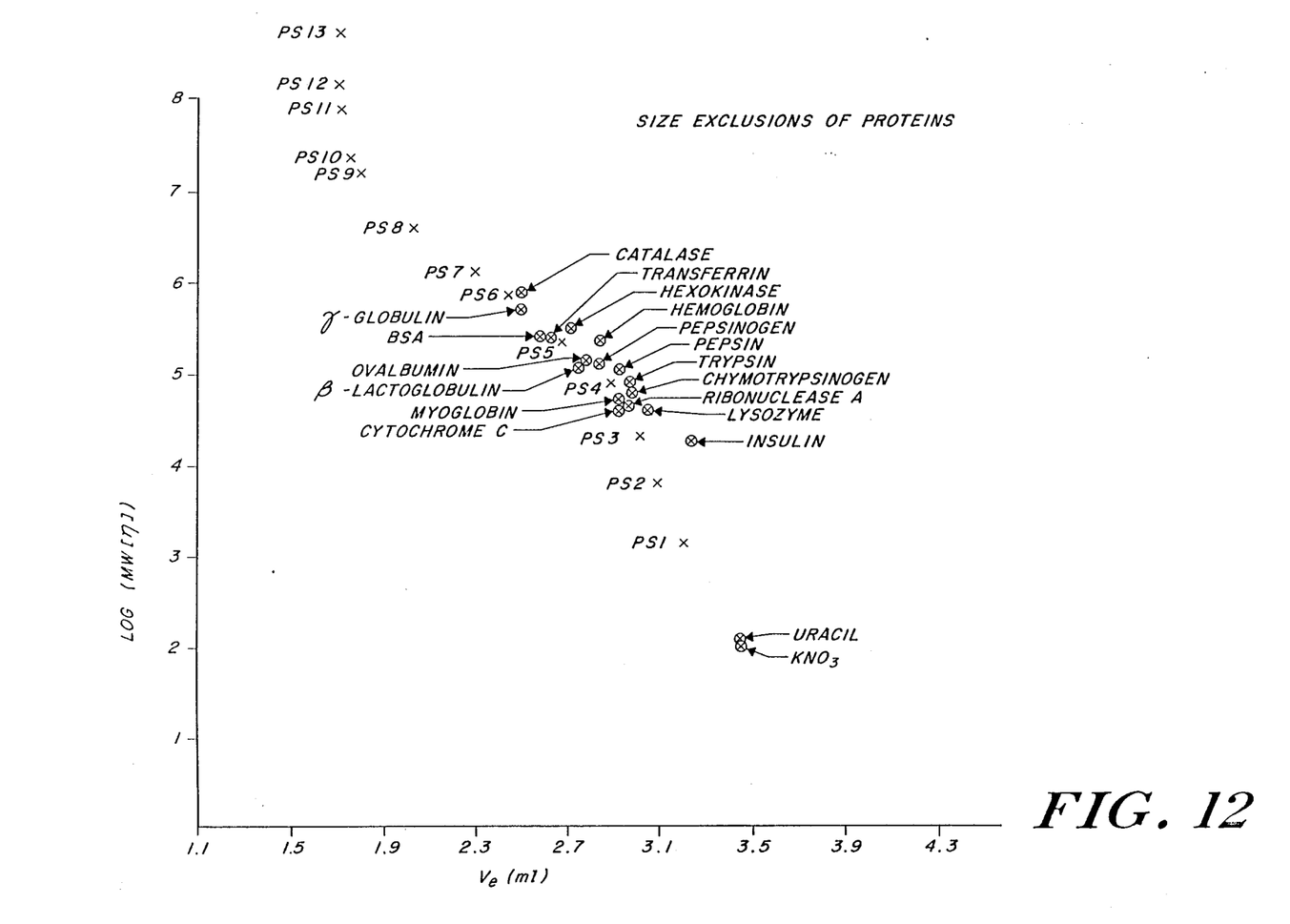
FIG. 12 is a plot of many proteins on a "universal" size exclusion calibration curve, demonstrating operation of the packing materials of the invention in a size exclusion chromatographic mode.

FIG. 12 shows a plot of the proteins of Table VIII on a polystyrene universal calibration. It is seen that the corrected values for the proteins fall generally on the polystyrene curve, in accordance with the hypothesis that size exclusion chromatography is occurring.

The invention is not to be limited by what has been particularly shown and described, except as indicated in the appended claims.

What is claimed is:

1. A method for bonding organosilanes to silica, comprising:
   coating the surface of silica particles with water;
   coating the surface of said water-coated silica particles uniformly with at least one alkoxysilane capable of forming at least two bonds to the silica surface via the silicon atom of the alkoxysilane; and
   heating the alkoxysilane-and-water-coated silica particles in the presence of vapors of a basic catalyst in the absence of solvent, to cause the alkoxysilane to react with the silica surface.

2. A method for bonding organosilanes to silica particles, comprising:
   equilibrating silica particles with water vapor in an atmosphere of constant relative humidity;
   adding to the water-equilibrated silica particles a solution of at least one alkoxysilane capable of forming at least two bonds to the silica surface via the silicon atom, in an organic solvent;
   removing said organic solvent, to leave silica particles coated with alkoxysilane and water;
   admitting vapors of a low molecular weight amine to the system; and
   heating the alkoxysilane-and-water-coated silica in the presence of said amine to cause the alkoxysilane to bond to the silica surface.

3. A method for bonding organosilanes to silica particles, comprising:
   equilibrating silica particles with water vapor in an atmosphere of low constant relative humidity;
   adding to the water-equilibrated silica particles a solution of at least one trialkoxysilane in a suitable organic solvent;
   removing the solvent by evaporation under reduced pressure to leave silica coated with trialkoxysilane and water;
   admitting vapors of ammonia to the system; and
   heating the trialkoxysilane-and-water-coated silica in the presence of said ammonia vapors, to cause the trialkoxysilane to react with the silica surface.

4. The method of claim 1 wherein said step of coating with water is carried out by equilibrating said silica particles with water vapor.

5. The method of claim 4 wherein said water vapor is in an atmosphere of constant relative humidity.

6. The method of claim 5 wherein said relative humidity is approximately 15%.

7. The method of claim 1 wherein said surface of said silica particles is coated with approximately 10–40 micromoles of water per square meter of said surface.

8. The method of claim 1 wherein said step of coating with alkoxysilane is carried out by adding to said water-coated silica particles a solution of said alkoxysilane in organic solvent, then removing said organic solvent.

9. The method of claim 8 wherein said organic solvent is removed by evaporation under reduced pressure.

10. The method of claim 1 wherein said surface of said silica particles is coated with said alkoxysilane in an amount ranging from about 1 equivalent to about 5 equivalents of alkoxysilane per unit area of said surface relative to the number of silanol groups per unit area of said surface.

11. The method of claim 1 wherein said alkoxysilane is a trialkoxysilane.

12. The method of claim 1 wherein said basic catalyst is an amine.

13. The method of claim 12 wherein said amine is ammonia.

14. The method of claim 2 wherein said equilibrating step said relative humidity is approximately 15%.

15. The method of claim 2 wherein said surface of said silica particles is coated with approximately 10–40 micromoles of water per square meter of said surface.

16. The method of claim 2 wherein in said removing step said organic solvent is removed by evaporation under reduced pressure.

17. The method of claim 2 wherein said surface of said silica particles is coated with said alkoxysilane in an amount ranging from about 1 equivalent to about 5 equivalents of alkoxysilane per unit area of said surface relative to the number of silanol groups per unit area of said surface.

18. The method of claim 2 wherein said alkoxysilane is a trialkoxysilane.

19. The method of claim 2 wherein said amine is ammonia.

* * * * *